United States Patent
Egnelöv

(12) 
(10) Patent No.: US 8,105,352 B2
(45) Date of Patent: Jan. 31, 2012

(54) MEDICAL SEALING DEVICE

(75) Inventor: Per Egnelöv, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 1178 days.

(21) Appl. No.: 11/302,519

(22) Filed: Dec. 14, 2005

(65) Prior Publication Data
US 2006/0142797 A1 Jun. 29, 2006

Related U.S. Application Data

(60) Provisional application No. 60/636,104, filed on Dec. 16, 2004.

(51) Int. Cl.
*A61B 17/08* (2006.01)
(52) U.S. Cl. .......................... 606/213; 606/215
(58) Field of Classification Search ................ 606/213, 606/232, 215, 233
See application file for complete search history.

(56) References Cited

U.S. PATENT DOCUMENTS

| | | | |
|---|---|---|---|
| 5,342,393 A | 8/1994 | Stack | |
| 5,350,399 A * | 9/1994 | Erlebacher et al. | 606/213 |
| 5,383,897 A | 1/1995 | Wholey | |
| 5,571,181 A * | 11/1996 | Li | 623/23.75 |
| 5,593,422 A | 1/1997 | Muijs Van De Moer et al. | |
| 5,620,461 A | 4/1997 | Muijs Van De Moer et al. | |
| 5,662,681 A | 9/1997 | Nash et al. | |
| 5,683,411 A | 11/1997 | Kavteladze et al. | |
| 6,315,787 B1 | 11/2001 | Tsugita et al. | |
| 6,475,213 B1 * | 11/2002 | Whayne et al. | 606/34 |
| 6,508,828 B1 | 1/2003 | Akerfeldt et al. | |
| 6,596,012 B2 | 7/2003 | Akerfeldt et al. | |
| 6,752,813 B2 * | 6/2004 | Goldfarb et al. | 606/139 |
| 6,929,655 B2 | 8/2005 | Egnelöv et al. | |
| 6,645,225 B1 | 11/2005 | Atkinson | |
| 2003/0014075 A1 * | 1/2003 | Rosenbluth et al. | 606/213 |
| 2004/0093025 A1 | 5/2004 | Egnelov | |
| 2004/0254596 A1 | 12/2004 | Kuester, III | |
| 2005/0228442 A1 | 10/2005 | Wheatley et al. | |
| 2008/0114395 A1 | 5/2008 | Mathisen et al. | |

FOREIGN PATENT DOCUMENTS

| | | |
|---|---|---|
| EP | 1 169 968 B1 | 1/2002 |
| WO | WO 94/28800 A1 | 12/1994 |
| WO | WO 95/20916 A1 | 8/1995 |
| WO | WO 98/31287 A1 | 7/1998 |
| WO | WO 03/094750 A1 | 11/2003 |
| WO | WO 2004/012603 A2 | 2/2004 |

(Continued)

OTHER PUBLICATIONS

Torbjorn Mathisen, U.S. PTO Office Action, U.S. Appl. No. 11/813,328, dated Nov. 17, 2009, 9 pgs.

(Continued)

*Primary Examiner* — Tuan Nguyen
(74) *Attorney, Agent, or Firm* — Foley & Lardner LLP

(57) ABSTRACT

A medical sealing device for the sealing of a puncture hole in a vessel wall includes an inner member, which is adapted to be positioned at an interior surface of the vessel wall, and an outer member, which is adapted to be positioned outside the vessel wall, the inner member and the outer member being held together by a retaining member. The sealing device further includes a sealing element, which is adapted to be positioned between the vessel wall and the outer member to improve the sealing performance of the sealing device.

24 Claims, 1 Drawing Sheet

FOREIGN PATENT DOCUMENTS

WO     WO 2005/002451 A1     1/2005

OTHER PUBLICATIONS

Torbjorn Mathisen, U.S. PTO Office Action, U.S. Appl. No. 11/813,328, dated Apr. 27, 2010, 8 pgs.

Torbjorn Mathisen, U.S. PTO Office Action, U.S. Appl. No. 11/813,328, dated Oct. 14, 2010, 9 pgs.

Torbjorn Mathisen et al., USPTO Office Action, U.S. Appl. No. 11/813,328, Oct, 6, 2011, 12 pages.

\* cited by examiner

MEDICAL SEALING DEVICE

The applicant claims the benefit of priority of U.S. Provisional Application No. 60/636,104, filed Dec. 16, 2004, whose entire contents are incorporated herein by reference.

FIELD OF THE INVENTION

The present invention relates generally to the field of sealing devices for the sealing of a percutaneous puncture in a vessel (or cavity) wall, and in particular to the class of sealing devices that comprises an intra-arterial member and an extra-arterial member, which sandwich the vessel wall and are held together by a retaining member, and more particularly to a sealing element which is positioned between the extra-arterial member and the vessel wall to improve the sealing performance of the sealing device.

BACKGROUND OF THE INVENTION

In the U.S. Pat. No. 6,508,828, which is assigned to the present assignee, a sealing device is disclosed for sealing a puncture hole in a vessel wall. The sealing device comprises an inner sealing member, an outer member, and a retaining member. The inner sealing member is adapted to be positioned at the inner wall of a vessel, while the outer member is adapted to be positioned at the outer wall of the vessel. In use, the inner and outer members sandwich the vessel wall, and are held together by the retaining member to thereby seal the puncture hole in the vessel wall.

In U.S. Pat. No. 6,596,012, which also is assigned to the present assignee, it is described how the sealing action of an inner sealing member can be improved by providing the inner sealing member with a rim portion that has a lower structural rigidity than a central portion of the inner sealing member. The entire contents of the '828 and '012 patents are incorporated herein, including the description of the various techniques, procedures, and devices therein.

Other examples of sealing devices that comprise an inner member and an outer member, which are held together by an elongated retaining member, such as a suture or filament, can be found in, for example, U.S. Pat. Nos. 5,593,422 and 5,620,461.

In U.S. Pat. No. 5,342,393, the retaining member is in the form of a stem that extends from the inner member.

SUMMARY OF THE INVENTION

Although at least a sealing device designed according to the teachings of U.S. Pat. Nos. 6,508,828 and 6,596,012 in practice has proven to work very well, its sealing function can be improved. One object of the present invention is therefore to provide a sealing device with an enhanced sealing ability. Preferably, the invention should be applicable to an existing sealing device without changing the design of the other components of the sealing device, or changing the practical handling of the sealing device.

The present invention is related to a sealing device comprising an intra-arterial (inner) member and an extra-arterial (outer) member, which are held together by a retaining member. In use, the inner member is introduced into the lumen of the vessel through a puncture hole in a vessel wall, and is then retracted until it is in close contact with the inner vessel wall. The retaining member, which is attached to the inner member, then extends through the puncture hole and holds the inner member tightly in a fixed position. The outer member is then advanced along the retaining member until the outer member is contacting the outside of the vessel wall. When the operation is completed, the outer and inner members will thereby sandwich the vessel wall and the puncture hole therein.

The actual sealing of the puncture hole can in principle be accomplished by two different mechanisms, either by clamping the vessel wall between the inner and outer members, or by the inner member alone. In the latter case, the outer member merely acts as a locking disc, which holds the inner sealing member in place. For the purpose of the present invention, it is not important which one of these two effects actually accomplishes the sealing of the puncture hole. (For the sake of completeness, a sealing device comprising an intra-arterial anchor member and an extra-arterial sealing member, such that the sealing is accomplished outside the vessel wall, is not considered to fall within the scope of the present invention.)

According to the invention, the sealing performance of a sealing device comprising an inner member, an outer member and a retaining member can be improved by providing a sealing element which is adapted to be positioned between the outer member and an outer wall of a vessel. The sealing element will thereby act as a washer or packing that supports the normal sealing action of the outer and inner members.

The sealing element should preferably be made from a soft and pliable material that conforms to the tissue surrounding the vessel. It is further preferred that the material be a bioresorbable material that resorbs in a patient's body. In one embodiment of the present invention, the sealing element exhibits an open porous structure.

In another embodiment of the invention, the sealing element comprises a haemostatic agent which promotes the sealing of a puncture wound in a vessel wall. The haemostatic agent can be provided as an exterior layer, or can be incorporated in the matrix of a porous material.

DETAILED DESCRIPTION OF EMBODIMENTS OF THE INVENTION

Figure 1:
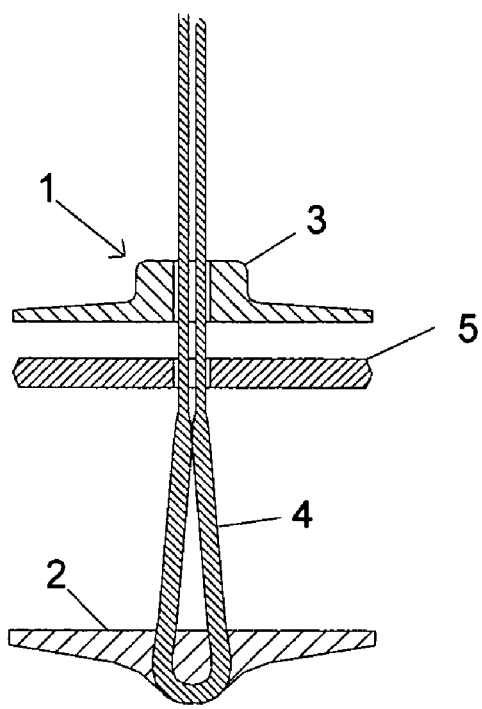
FIG. 1 is a schematic illustration of the components of a sealing device according to the present invention.

A sealing or closure device 1 according to one embodiment of the present invention is schematically illustrated in FIG. 1. The sealing device 1 comprises an inner member 2 and an outer member 3, which are held together by an elongated retaining member 4. The retaining member 4 can be looped through the inner member 2, as shown in FIG. 1. In addition, the retaining member 4 can be smaller in width at the outer member 3 than at the inner member 2. Further, the retaining member 4 can be a single unitary piece with a first portion and a second portion having an enlarged thickness which is larger in cross section than the first portion. The inner member 2, the outer member 3 and the retaining member 4 are all of previously known designs, examples of which can be found in the above-referenced patents. The retaining member 4 is attached to the inner member 2, and extends through a hole in the outer member 3. During the positioning operation of the sealing device 1, the outer member 3 can thereby slide along the retaining member 4 into abutment against the outer surface of a vessel. Unlike the previously known sealing devices, the sealing device 1 comprises further an extra sealing element 5, which in this example has the form of a relatively thin sealing disc or washer 5.

Figure 2:
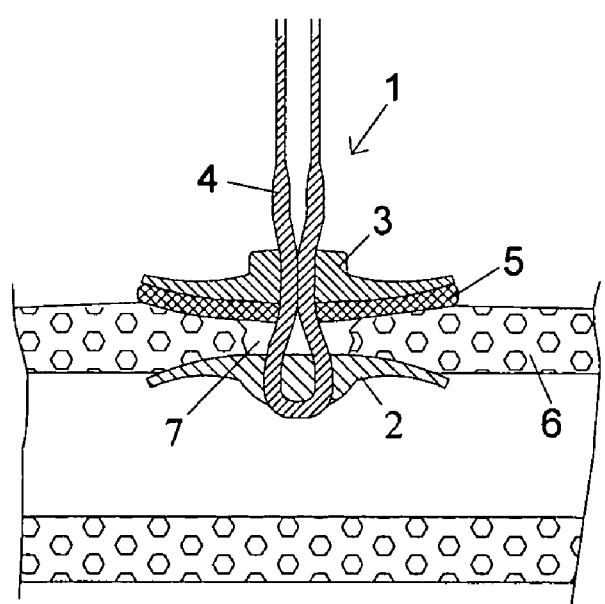
FIG. 2 shows the sealing device of FIG. 1 in a state corresponding to the completion of a medical sealing operation.

The function of the sealing disc 5 is clearly shown in FIG. 2, where the sealing device 1 has been positioned around a vessel wall 6 in order to close a puncture hole 7 therein. The figure illustrates that the inner member 2 is positioned at an interior surface of the vessel wall 6, while the outer member 3 is positioned at an exterior surface of the vessel wall 6, and that the retaining member 4 extends through the puncture hole 7 in the vessel wall 6, such that the vessel wall 6 is sandwiched between the inner member 2 and the outer member 3. In this example, a portion of the retaining member 4 has been provided with an enlarged thickness, such that the outer member 3 is held in a fixed position by the friction acting between the retaining member 4 and the outer member 3. It should, however, be understood that other ways of securing an outer member to a retaining member could be provided, for example by having a retaining member in the form of a saw-toothed stem. Although not shown in the figures, it is preferred that the curvatures of the inner and outer members are adapted to the curvature of the vessel wall.

In the example shown in FIGS. 1 and 2, a sealing element 5 has been provided as a separate part of sealing device 1. It is, however, also contemplated—and considered to fall within the scope of the present invention—that an extra sealing member can be a more integrated part of a sealing device. A sealing element can, for example, be attached to an outer member by means of a suitable adhesive.

A sealing element, such as the sealing disc 5 shown in FIGS. 1 and 2, is preferably made from a soft and pliable material that conforms to the shape and texture of the vessel wall. The sealing element will thereby act as a packing or seal that mechanically prevents (or minimizes) leakage between an outer member and the vessel wall. Such a leakage could otherwise arise from the forming of small canals between a sealing or closure device and the tissue around a puncture wound. A sealing element according to the present invention is relatively thin and has a thickness that is comparable to the thicknesses of the inner and outer members. The thickness is preferably less than 5 mm, and more preferably 3-4 mm. As an alternative, a sealing element could have a non-uniform thickness, with for example a larger thickness in the centre of the sealing element than at its periphery. The central portion could then be arranged as a cone-shaped structure that can protrude a short distance into a hole in a vessel wall. Preferably, the diameter of a sealing element is essentially equal to the diameter of an outer member.

To guarantee a high degree of compliance, a sealing element can be made from a material that exhibits an open porous structure. The porosity of the material could be in the range from 50 to 90 percent. By making the sealing element from a porous material, the compliance of the sealing element could be modified by modifying the porosity of the material—in addition to modifying the material composition itself. If a sealing element is provided as an integrated part of an outer member, the outer member could be made from a homogenous material, whereas the sealing element can be made from a porous material. Preferably, an outer assembly, which consists of an outer member and a sealing element, would then have a continuous transition from a homogenous structure to an open porous structure in the direction towards a vessel wall.

Whether or not the material in the sealing element exhibits a porous structure, the material should preferably be a bioresorbable material. To allow a close adaptation to the surrounding tissue, the material structure should be able to accommodate large deformations without breaking, and should therefore have a glass transition temperature below room temperature. Non-limiting examples of such synthetic resorbable materials are various combinations of the monomers glycolide, lactide (all stereoismers), trimethylene carbonate, ε-caprolactone, dioxanone or dioxepanone. Depending on the desired mechanical properties and the choice of manufacturing method, several of the homopolymers or copolymers containing two or more of the above-mentioned monomers can be used to manufacture a sealing element, including a porous sealing element. Other examples of synthetic resorbable polymers that can be utilized are various aliphatic polyurethanes, such as polyureaurethanes, polyesterurethanes and polycarbonateurethanes, and yet other materials such as polyphosphazenes or polyorthoesters.

The sealing element, including a porous sealing element, can also be made from natural biomaterials. Several resorbable and naturally occurring materials exist that will fulfill the requirements above. Non-limiting examples of suitable natural biomaterials are various forms of collagen, hyaluronic acid, alginic acid, fibrin, starch and hemicelluloses.

An open porous structure can be fabricated with a plurality of different known techniques, including leaching of added components, such as salt, thermally or chemically induced phase separation techniques, and sublimation.

In yet another embodiment of the present invention, a sealing element is supplemented with a haemostatic agent, which promotes the coagulation process. In addition to its mechanical sealing properties, the sealing element then acts as a substrate or carrier material for the haemostatic agent. If the sealing element comprises an open porous structure, the haemostatic agent can be incorporated in the matrix structure. If the sealing element instead is made from a non-porous material, the sealing element can be coated with the haemostatic agent, which then is provided as a thin layer. Suitable haemostatic agents are exemplified by, but not limited to, thrombin, pro-thrombin, coagulation factor XIIa, factor Va, factor Xa, or tranexamic acid.

Although the present invention has been described with reference to specific embodiments, also shown in the appended drawings, it will be apparent to those skilled in the art that many variations and modifications can be made within the scope of the invention as described in the specification and defined with reference to the claims below.

What is claimed is:

1. A medical sealing device for sealing of a puncture hole in a vessel wall, comprising:
    an inner member, which is adapted to be positioned at an interior surface of the vessel wall;
    an outer member, which is adapted to be positioned outside the vessel wall; and
    the inner member and the outer member being held together by a retaining member;
    wherein the sealing device further comprises a sealing element, which is adapted to be positioned between the vessel wall and the outer member,
    wherein a portion of the retaining member has an enlarged thickness that engages with the outer member to hold the outer member in a fixed position when the medical sealing device is used to seal the puncture hole in the vessel wall,
    wherein the outer member is moveable with respect to the inner member along the retaining member,
    wherein the sealing element has a larger thickness in a central portion than in a peripheral portion,
    wherein the outer member has a larger thickness in a central portion than in a peripheral portion.

2. A medical sealing device according to claim 1, wherein a diameter of the sealing element is essentially equal to a diameter of the outer member.

3. A medical sealing device according to claim 1, wherein an overall thickness of the sealing element is less than 5 mm.

4. A medical sealing device according to claim 1, wherein the sealing element is a separate part in relation to the outer member.

5. A medical sealing device according to claim 1, wherein the sealing element is an integrated part of the outer member.

6. A medical sealing device according to claim 1, wherein the sealing element is made of a soft and compliable material.

7. A medical sealing device according to claim 1, wherein the sealing element is made of a bioresorbable material.

8. A medical sealing device according to claim 1, wherein the medical sealing device is made of a porous material.

9. A medical sealing device according to claim 8, wherein the porosity of the material ranges from 50 to 95 percent.

10. A medical sealing device according to claim 1, wherein the sealing element is made from glycolide, lactide, trimethylene carbonate, ε-caprolactone, dioxanone, dioxepanone, polyurethane, polyphosphazenes, polyorthoesters, collagen, hyaluronic acid, alginic acid, fibrin, starch or hemicellulose, or a combination thereof.

11. A medical sealing device according to claim 1, wherein the sealing element further comprises a haemostatic agent.

12. A medical sealing device according to claim 11, wherein the haemostatic agent is from the group comprising thrombin, pro-thrombin, coagulation factor XIIa, factor Va, factor Xa, or tranexamic acid.

13. A medical sealing device according to claim 1, wherein the inner member is a seal.

14. A medical sealing device according to claim 1, wherein the retaining member extends through at least one hole in the outer member.

15. A medical sealing device according to claim 1, wherein the retaining member extends through at least one hole in the inner member.

16. A medical sealing device according to claim 1, wherein the retaining member is looped through the inner member.

17. A medical sealing device according to claim 1, wherein the medical sealing device is configured such that the outer member can slide along the retaining member.

18. A medical sealing device according to claim 1, wherein the retaining member connects the inner member, the outer member, and the sealing element, wherein the retaining member is smaller in width at the outer member than at the inner member.

19. A medical sealing device according to claim 1, wherein the inner and outer members are separate pieces that move relative to one another.

20. A medical sealing device according to claim 1, wherein the retaining member is a suture.

21. A medical sealing device according to claim 1, wherein the retaining member is a single unitary piece with a first portion and second portion, wherein the second portion includes the enlarged thickness, which is larger in cross section than the first portion.

22. A medical sealing device according to claim 1, wherein the sealing element is moveable with respect to the inner member.

23. A medical sealing device according to claim 1, wherein the sealing element is moveable with respect to the outer member.

24. A medical sealing device according to claim 1, wherein the retaining member consists of suture material.

* * * * *